United States Patent [19]

Kolobow

[11] Patent Number: 4,889,137
[45] Date of Patent: Dec. 26, 1989

[54] METHOD FOR IMPROVED USE OF HEART/LUNG MACHINE

[75] Inventor: Theodor Kolobow, Rockville, Md.

[73] Assignee: The United States of America as reprsented by the Department of Health and Human Services, Washington, D.C.

[21] Appl. No.: 190,627

[22] Filed: May 5, 1988

[51] Int. Cl.[4] .............................................. A61B 17/00
[52] U.S. Cl. .................................... 128/898; 606/191; 606/194; 600/16
[58] Field of Search ..................... 128/341, 344, 348.1, 128/898; 600/16, 17, 18

[56] References Cited

U.S. PATENT DOCUMENTS

| | | |
|---|---|---|
| 707,775 | 8/1902 | Harris . |
| 4,143,425 | 3/1979 | Runge . |
| 4,183,102 | 1/1980 | Guiset .............................. 128/344 X |
| 4,382,445 | 5/1983 | Sommers . |
| 4,503,569 | 3/1985 | Dotter . |
| 4,531,933 | 7/1985 | Norton . |
| 4,553,532 | 11/1985 | Bohls . |
| 4,553,545 | 11/1985 | Maass et al. ........................ 128/341 |
| 4,592,340 | 6/1986 | Boyles . |
| 4,653,496 | 3/1987 | Bundy . |
| 4,665,918 | 5/1987 | Garza . |
| 4,666,443 | 5/1987 | Portner . |
| 4,681,570 | 7/1987 | Dalton . |
| 4,705,507 | 11/1987 | Boyles . |
| 4,718,907 | 1/1988 | Karwoski . |
| 4,721,115 | 1/1988 | Owens . |
| 4,762,130 | 8/1988 | Fogarty et al. . |
| 4,771,765 | 9/1988 | Choy et al. . |
| 4,813,925 | 3/1989 | Anderson, Jr. . |

Primary Examiner—Michael H. Thaler
Attorney, Agent, or Firm—Browdy and Neimark

[57] ABSTRACT

Long term closed chest partial and total cardiopulmonary bypass by peripheral cannulation for severe right and/or left ventricular failure is achieved by the use of a percutaneous coil positioned in the pulmonary artery across the pulmonary artery valve to decompress the left heart.

7 Claims, 2 Drawing Sheets

METHOD FOR IMPROVED USE OF HEART/LUNG MACHINE

FIELD OF INVENTION

The present invention relates to improvements in cardiopulmonary bypass; and, more particularly, it relates to a method and means for effecting heart assist through peripheral cannulation alone.

BACKGROUND OF THE INVENTION

It has long been recognized that venous-arterial bypass with a membrane lung, also called ECMO (extracorporeal membrane oxygenation), is a reasonable option to assist a failing heart, except that there continues to be no really satisfactory way to decompress the left heart. To overcome this handicap, it has been proposed to decompress the left atrium by a large catheter passed into the vena cava, and puncturing the interatrial septum. An alternative suggested was to pass a large bore catheter through the aorta across the aortic valve into the left ventricle. Both such proposals carry substantial morbidity.

As a possible alternative, mechanical means can be used to assist the failing circulation; however, this require implantation, e.g. one or two blood pumps which in turn requires the opening of the chest. Upon recovery, the chest must be again opened to remove the blood pumps. In addition, such implantation is time consuming, it entails a major commitment, and is very high in cost. A major complication related to this practice is bleeding, and infection occurs in over one-half of the patients so treated.

In another context, coil spring devices are known for use in supporting damaged blood vessels to prevent them from collapsing. It has been proposed to make these coils from so-called memory metal (Nitinol) noting the Dotter U.S. Pat. No. 4,503,569; also see U.S. Pat. No. 3,868,956. In Maass et al U.S. Pat. No. 4,553,545, various shapes and configurations are suggested whereby the coil can be expanded from a smaller diameter state to a larger diameter state, again for the purpose of preventing damaged blood vessels and the like from collapsing.

SUMMARY OF THE INVENTION

It is, accordingly, an object of the present invention to overcome deficiencies in the prior art, such as mentioned above.

It is another object of the present invention to provide improvements in total and partial cardiopulmonary bypass.

It is a further object of the present invention to provide a method and means of effecting heart assist through peripheral cannulation without thoractomy.

It is yet another object of the invention to provide an improved method of rendering the pulmonary artery incompetent so as to allow successful decompression of the left heart during severe heart failure in order to conduct prolonged venous-arterial bypass using an artificial heart/lung machine.

It is still another object of the present invention to provide a new use for coil-spring like devices for the above purposes.

It is yet a further object of the present invention to provide special coil devices especially adapted for the above purposes.

These and other objects are achieved according to the present invention which relates to a system of conducting total or partial heart assist through peripheral cannulation alone, not requiring thoractomy. This is achieved through the deployment of a special coil or spring-like device positioned within the pulmonary artery and across the pulmonary artery valve, the coil device serving to render the pulmonary artery incompetent so as to allow for the decompression of the left heart during severe heart failure. The left heart being decompressed, it becomes possible to conduct venous-arterial bypass using an artificial lung for hours, days or weeks until heart function recovers, or to allow thrombolytic agents sufficient time to open up clogged arteries and buy time for the heart to recover. Similarly, the device can be used as a bridge to heart transplantation. Such treatment is appropriate when there is partial or complete right and/or left heart failure, including ventricular fibrillation (total ceasation of all heart function).

The nature and advantages of the present invention will be more apparent from the following detailed description taking in conjunction with the drawings, wherein:

DETAILED DESCRIPTION OF EMBODIMENTS

Figure 4:
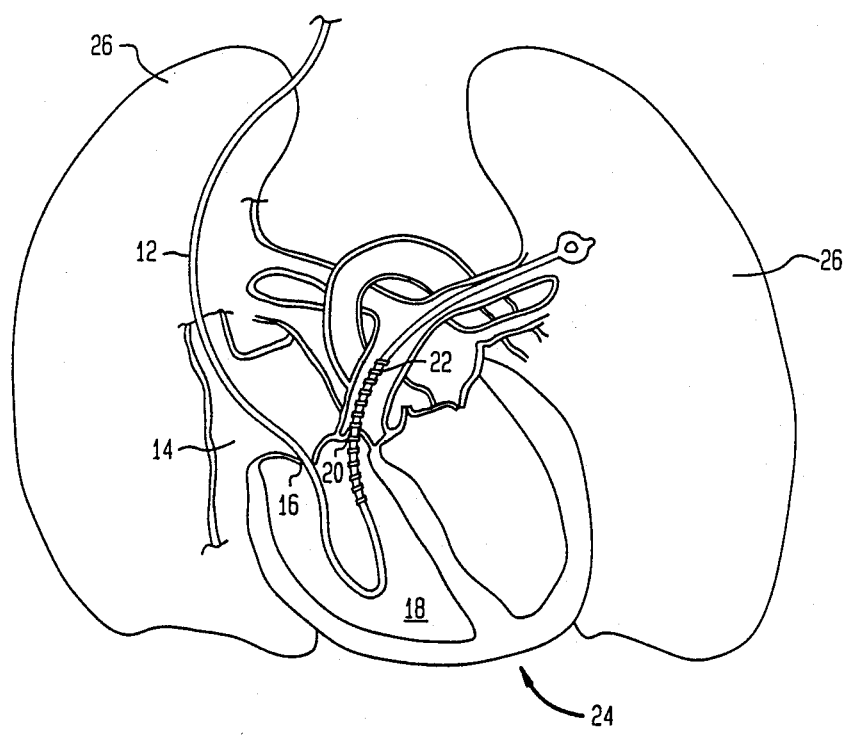
FIG. 4 is a partially schematic sectional view of the heart showing emplacement of a coil according to the present invention.

In accordance with the present invention, a coil or coiled-spring like element is threaded through the superior vena cava, then through the right atrioventricular valve and finally partway through the pulmonary trunk valve into the pulmonary artery where the coil device is preferably enlarged in diameter so as to keep the pulmonary valve open and to render the pulmonary artery incompetent. FIG. 4 shows such an operation with a coil 10 formed of a rectangular ribbon being carried on a catheter 12, the catheter having been threaded through the right atrium 14, the right atrioventricular valve 16 into the right ventricle 18 and then through the pulmonary trunk valve 20 and into the pulmonary artery 22. So as to provide a more complete illustration, the heart 24 is shown in conjunction the lungs 26.

In the illustration of FIG. 4, the coil 10 is retained on the catheter 12 in a fixed, floating or collapsed state so as to be able to be threaded into position. After reaching the illustrated position, the coil 10, if same is in a collapsed or fixed initial state, is released so as to expand to a second, enlarged state. To be able to accomplish this function, the coil needs to have a good memory and be made of a material which does not easily fatigue. It must also be easily distortable so that it can be collapsed into a smaller diameter. A variety of materials can be used including the polyester Hytrel, as well as polyurethane and silicone rubber. Elastomeric materials such as natural and synthetic rubbers or elastomeric plastics, and flexible plastics can be used, but in all cases the material of the coil should be provided with a surface which does not promote blood clotting, i.e. the coil is desirably coated with heparin or a heparin complex or the like.

Figure 1:
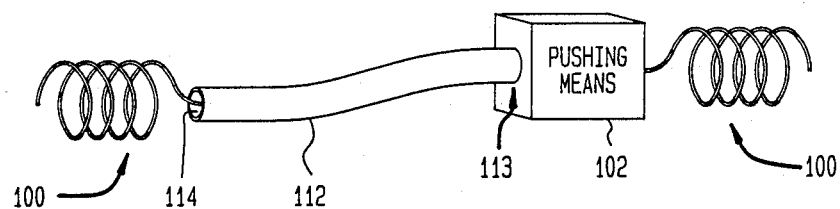
FIG. 1 is schematic view illustrating how to pass a relatively large coil through a narrow blood vessel for emplacement into the heart in accordance with the present invention.

FIG. 1 shows schematically another system for placing a relatively large diameter coil 100 through a relatively narrow blood vessel. This is accomplished by the use of a narrow hollow catheter 112 having an exterior sufficiently small to be threaded through the blood vessels to reach the position shown in FIG. 4. In this case the catheter 112 is provided at its distal end 113 with a suitable pushing means 102 which could, in a simple form, constitute a pair of a driven wheels through which the forward end of the coil 100 is passed. When the catheter 112 is threaded into the heart and reaches its desired location, the pushing means 102 is activated to push the coil through the catheter 112; when the coil 100 arrives downstream of the proximal end 114 of the catheter, the memory of the coil 100 allows it to expand to its normal enlarged diameter where it then serves its function rendering incompetent the pulmonary artery 22. It will be understood that pushing means could take other forms e.g. the pushing means can instead be a pulling means.

Other coil constructions and means for controlling the size of the coil which can be used according to the present invention are disclosed in the aforementioned Maass et al U.S. Pat. No. 4,553,545.

Figure 2A:
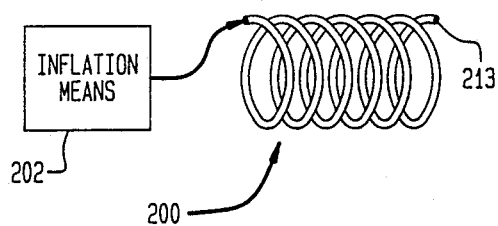
FIGS. 2A and 2B are enlarged schematic representations of another coil device according to the present invention, FIG. 2A showing such coil in a relatively small state, and FIG. 2B showing such coil in a relatively enlarged state.
Figure 2B:
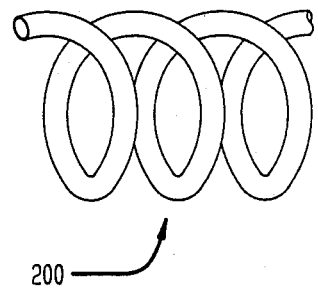

FIGS. 2A and 2B show another coil which is particularly suitable according to the present invention. FIG. 2A shows a coil 200 in the form of a hollow tube. Upstream from the distal end of the coil 200, desirably with a hollow catheter placed therebetween, is provided a suitable inflation means 202, such as a pump or an hydraulic piston. The proximal end 213 of the hollow coil 200 is sealed closed. FIG. 2A, which is greatly enlarged, illustrates the coil 200 in an uninflated condition, its overall diameter being such that it can be easily threaded through the blood vessels and into the position illustrated in FIG. 4. When that position is reached, the inflation means 202 is activated and the coil 200 is inflated, preferably by hydraulic fluid which also makes the coil 200 more rigid, and it then assumes an enlarged size as illustrated in FIG. 2B. When the time arrives to remove the coil 200, it is merely deflated by removal of the hydraulic or pneumatic fluid whereupon the coil 200 returns to its original size as shown in FIG. 2A.

It will be understood that in order to effect the embodiment of FIGS. 2A and 2B, the coil 200 needs to be formed of an elastomer such as polyurethane. The tubing which forms the coil 200 is also desirably reinforced within its wall with non-elastic fibers oriented in such a direction that inflation causes the coil to enlarge in diameter but not in length. The reinforcing fibers can be any suitable material, although Aramid (aromatic polyamide) or Kevlar fibers are particularly contemplated.

Figure 3:
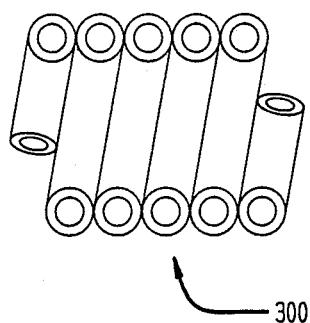
FIG. 3 is an enlarged sectional view of another coil device according to the present invention.

FIG. 3 illustrates a further variation similar to the embodiment of FIGS. 2A and 2B. FIG. 3 shows a coil 300 which, like the coil 200, is formed of an inflatable plastomer or elastomer. In the coil 300, however, the sidewall is fused or otherwise adhered along its connecting line so that the coils cannot separate. Upon inflation, the coil 300 will expand very little lengthwise and almost entirely in diameter, as desired. As with the coil 200, the device of FIG. 3 can be inflated either hydraulically or pneumatically, although hydraulic inflation is preferred so that in its inflated condition the coil 300 has not only a greater diameter than in its uninflated condition, but also is stiffer.

The invention will now be described in more detail with regard to certain specific embodiments of use, the following example being entirely illustrative.

EXAMPLE 1

A coil according to the present invention was used as follows.

Example 1 Summary

The right external jugular vein and the right subclavian artery were cannulated in two healthy sheep under general anesthesia. A spring coil according to the present invention was attached to a 7 F Swan Ganz catheter, and was positioned at the level of the pulmonary artery valve, rendering it partially incompetent. The extracorporeal circuit included a venous reservoir, a roller pump, a membrane lung and a blood pulsator set at 25 beats per minute. Ventricular fibrillation was induced with 110 VAC. Extracorporeal blood flow was raised to 110-120 ml/kg/min. Mechanical pulmonary ventilation was charged to 5% $CO_2$ in room air.

During bypass the wedge pressure averaged 8-10 mmHg, pulmonary artery pressure 5-8 mmHg, and the central venous pressure 2-mmHg. After 38 and 48 hours respectively, the hearts were defibrillated with DC shock. There was total heart failure with no ejection from right or left. Total cardiopulmonary bypass was continued. The right heart recovered after one and three hours, respectively. After three and seven hours respectively, there was some aortic ejection.

By 16 and 18 hours, respectively, the sheep were off bypass and on room air, with return to baseline cardiac function.

Throughout the recovery, the wedge pressure averaged 4-8 mmHg. At autopsy, all hearts were soft, normal in appearance. Histological examination of the lungs and hearts was unremarkable. On the basis of this example, it is concluded that the coil within the pulmonary artery readily decompressed the LV. Ventilating lungs with 5% carbon dioxide in air during cardiopulmonary bypass sustained excellent lung function. This technique provides a rapid and effective means for long term right and/or left heart assist without thoracotomy.

The size of the coil will, of course, depend on the size of the patient. For sheep, the coil was about 12 cm long, whereas for humans a desirable length is 3-8 cm. The currently preferred device consists of a flat plastic spring of approximately six turns per inch, fixed to a Swan Ganz flow directed catheter as illustrated in FIG. 4. In this case, the flat material from which the coil is formed has a thickness of 0.015 inches and a width of 0.150 inches. As indicated above, the spring need not be flat, but can be made of material having a round cross section. Also as indicated above, the coils can be made of various snappy plastics, such as Hytrel elastomeric polyester, or of memory metal such as Nitinol.

As noted above, the system of the present invention permits elimination of relatively invasive methods such as thoracotomy. During the past decade, the relative safety and efficacy of temporary left heart assist devices has been well established. Temporary cardiac support is indicated for patients in whom some recovery of cardiac function is expected following a period of cardiac assist, or as a bridge to heart transplantation. In the former situation, the goal is to augment the failing ventricles, while in the latter case the goal is to provide hemodynamic support until a donor organ becomes available. Whereas previously available cardiac assist devices for total or near total cardiac assist relied heavily on invasive methods including thoracotomy, such methods are avoided according to the present invention which achieves partial or total cardiac assistance through peripheral cannulation alone. The method is similar to conventional cardiopulmonary bypass except that decompression of the left heart is obtained by positioning the coil within the pulmonary artery valve thereby rendering it at least partially incompetent. Furthermore, to protect the lungs during periods of total or near total cardiopulmonary bypass, the lungs are ventilated with a mixture of 5% carbon dioxide and room air.

Example 1 above shows that, using the model of heart failure induced by prolonged ventricular fibrillation, right or left heart failure or total heart failure can be effectively supported according to the present invention, and that following the procedure there is a recovery of cardiac function with no impairment in pulmonary function.

Example 1 Discussion

The coil used in Example 1 was a fixed spring made of a flat ribbon of Hytrel elastomeric polyester of 0.25 mm thickness, and 3.5 mm width. The ribbon was coiled into a spring with 2-3 mm gaps between each turn, with a total finished length of 6-10 cm. For reduced thrombogenicity, the spring was treated with TDMAC complex, which is a heparin complex.

The extracorporeal heart assist system included a 1.2 cm internal diameter silicone rubber tubing through which blood flowed to an electromagnetic flow probe, a flow through oximeter and finally into a 120 ml capacity venous reservoir, the latter of which was connected to a micro switch to sense venous return and to control blood pumping. The blood was then pumped by a roller pump through a 3.5 m2 membrane lung and then flowed into two cylindrical 80 ml capacity silicone rubber reservoirs, separated from each other by a unidirectional (prosthetic cardiac) valve. The second of these reservoirs was alternatingly pressurized with air at a rate of 25-40 pulses per minute to cause ejection at a pressure of 300-600 mm Hg into the arterial return line. The stroke volume varied from 60 to 80 ml. An humidified mixture of air and oxygen at 38° C. was passed through the membrane lung at a flow rate sufficient to maintain $PaCO_2$ within the baseline range of 2-3 liters per minute. The entire perfusion system was placed into a thermostatically controlled chamber, maintained at 39° C.

Healthy sheep weighing 14 and 16.5 kg. were used. As indicated above, the coil mounted on a 7 Swan Ganz catheter was placed within the lumen of the pulmonary artery valve, rendering the valve partially incompetent. A small teflon catheter was placed into the left common carotid artery for arterial pressure monitoring and for arterial blood sampling. Following total body heparinization with 300 u/kg, a 6.5 mm internal diameter reinforced polyurethane catheter was inserted through the right external jugular vein with the drainage orifice at about the level of the right atrium. The arterial return catheter was introduced into the right subclavian artery with a terminal end that rested within the artery. The sheep were then placed on mechanical ventilation at a respiratory rate of 15-16 pulses per minute, a tidal volume of 10-12 ml/kg, with an inspiratory to expiratory ratio of 1:2, a positive and expiratory pressure of 4 $cmH_2O$, F102 0.40, and a peak inspiratory pressure of 15-17 $cmH_2O$.

After two hours of such ventilation, baseline respiratory and hemodynamic readings were obtained. The extracorporeal perfusion circuit was first primed with heparinized normal saline, using the carbon dioxide priming technique. Just before going on bypass, all saline was displaced with freshly drawn heparinized whole blood.

Partial VA bypass was then begun at a flow rate of 50-60 ml/kg/min. The ACT time was monitored and sufficient heparine was administered to keep the ACT between 200 and 250 sec.

Once the hemodynamic status became stable and the body temperature reached 37° C., ventricular fibrillation was induced by a single 110 VAC shock across the chest. The extracorporeal blood flow was raised to a 110-120 ml/kg/min. Immediately, the gas mixture to the mechanical ventilator was changed from room air to a mixture of room air with 5% carbon dioxide added, and the VT was reduced to 7-8 ml/kg.

During the total cardiopulmonary bypass, frequent blood gas measurements were taken. Unlike during baseline conditions, the pulmonary blood flow during the total cardiopulmonary bypass reversed. Blood from bronchial veins, Thebesian veins, sinusoidal drainage, etc., drain in the reverse direction, through the lungs and then into the pulmonary artery through the open pulmonary valve which is kept open by the coil and then into the right ventricle and into the right atrium.

Following two days of total coronary pulmonary bypass, the hearts were defibrillated with DC shock. There was some ejection by the right ventricle, but none by left ventricle. Total cardiopulmonary bypass was continued as long as there was no measurable LV ejection. The extracorporeal blood flow was reduced as ejection became evident. After recovery of right and left heart functions, bypass was discontinued and anesthesia was stopped. The sheep were weaned to intermittent mandatory ventilation and continuous positive air wave pressure on room air. Lastly, the sheep were returned to baseline conditions of continuous positive pressure ventilation for final respiratory and hemodynamic function measurements. Following this the sheeps were sacrificed with intravenous injection of sodium pentobarbital.

The general appearance of the lungs was observed during autopsy, as well as the general appearance of epicardium and the endocardium, and of sections of the right and left ventricles. The heart was then fixed with 2% glutaraldehyde. The hearts were soft and normal in appearance and the lungs pink and well airated. Histological examination showed no alteration or areas of infarction.

Introduction of the coil into the pulmonary valve appeared to have no noticeable adverse effects. On the contrary, the procedure permitted total cardiopulmonary bypass without much of the trauma usually associated therewith.

There is great merit to a system which can provide cardiac assistance through peripheral cannulation, and this is particularly so if such system is capable of addressing both moderate and total cardiac failure. Such a system avoids current highly invasive techniques including thoracotomy and the implantation of two or more large conduits, or the implantation of assist devices. The present invention thus eliminates risks inherent in the current invasive techniques including infection, impaired lung function and bleeding.

In a clinical setting, total cardiopulmonary bypass is routinely used numerous times a day throughout the world in cardiac surgery. While total cardiopulmonary bypass provides total cardiac assistance, two factors limit its use for cardiac assistance in medical and surgical settings: first, an increase in extracorporeal bypass raises systemic blood pressure, and increases systemic circulation. Invariably, such an effect also raises the afterload, increasing left ventricular filling pressure, and further impairing cardiac function. This in turn can also lead to pulmonary edema. Second, during high flow cardiopulmonary bypass the pulmonary blood flow is severely reduced. Pulmonary hypoperfusion has been implicated in pulmonary dysfunction after short term periods of total cardiopulmonary bypass following cardiac surgery.

To overcome the above limitations, a number of issues had to be addressed to permit total cardiopulmonary bypass by peripheral cannulation alone for cardiac assist. The advent of low resistance large bore wire reinforced catheters provided the means to cope with the at times very large venous return to keep CVP within a normal range. However, control of left ventricular filling pressure during severe left ventricular failure required that the left heart be decompressed.

In this model of total cardiac failure (during induced ventricular fibrillation), the blood drained from the left side of the heart across the lungs into the pulmonary artery, and crossed the pulmonary valve and the tricuspic valve, and entered the right atrium without undue rise in the left atrium pressure during the first few hours. The retrograde blood flow later invariably rose causing an intolerable rise in left atrium pressure after 6–24 hours. At some point means had to be found to decompress the left atrium. Use of the coil as set forth above according to the present invention solves this problem.

Example 1 shows that the left heart can be readily decompressed by placement of a coil in the pulmonary artery extending across the pulmonary artery valve, while the heart is in ventricular fibrillation. Furthermore, following the fibrillation and by ventricular failure, the coil prevents any rise in wedge pressure, even where the right heart recovers first. Similarly, Example 1 shows immediate recovery in pulmonary function following stopping of the bypass, with the test animals immediately tolerating room air ventilation. The example shows that total cardiac assistance, right and/or left, can be provided by peripheral cannulation alone, provided a coil is inserted in the pulmonary artery across the pulmonary artery valve to decompress the left heart. With minimal invasion, such assistance can provide the time needed to recover from catastrophic cardiac events.

It is to be understood that the invention is not limited to the embodiments disclosed which are illustratively offered and that modifications may be made without departing from the invention.

What is claimed is:

1. A method of assisting cardiopulmonary bypass, comprising threading a coil through the right atrium, the right ventricle and into the pulmonary artery across the pulmonary artery valve to keep the pulmonary artery valve open during cardiopulmonary bypass.

2. A method according to claim 1 wherein said coil is maintained during said threading in a first condition wherein the diameter of said coil is small, and said coil is then changed to a second condition of increased diameter when said coil is positioned across the pulmonary artery valve.

3. A method according to claim 2 wherein said coil comprises a twisted hollow tubing closed at its distal end and formed of an elastomeric plastic or rubber, said method comprising inflating said tubing after said coil has been placed across the pulmonary artery valve to effect said increased diameter.

4. A method according to claim 3 wherein said tubing is reinforced so that upon said inflation thereof it inflates primarily to increase the diameter of said coil without substantially increasing the length thereof.

5. A method according to claim 3 wherein contacting surfaces of adjacent coil sections of said coil are fused or bonded together so that upon said inflation said coil enlarges primarily in a radial direction.

6. A method according to claim 1 wherein said coil comprises a twisted wire formed of elastomeric plastic or rubber having good memory, good anti-fatigue properties, being capable of being distorted and having sufficient rigidity to maintain the pulmonary artery valve open.

7. The method of claim 6, wherein said twisted wire is maintained in a flattened state within an axial bore of a catheter until said wire is proximal said pulmonary artery valve, said wire is then released from said catheter so as to expand to an enlarged state and lodge within said pulmonary artery valve to keep said pulmonary artery valve open.

* * * * *